United States Patent [19]

Favre et al.

[11] 4,154,583
[45] May 15, 1979

[54] AUTOMATED TEMPERATURE PROGRAMMED PREPARATIVE CHROMATOGRAPHY

[75] Inventors: John A. Favre; Lloyd E. Gardner, both of Bartlesville, Okla.

[73] Assignee: Phillips Petroleum Company, Bartlesville, Okla.

[21] Appl. No.: 845,182

[22] Filed: Oct. 25, 1977

[51] Int. Cl.² .................................. B01D 15/08
[52] U.S. Cl. .................................. 55/67; 55/197; 55/208; 210/31 C; 210/198 C
[58] Field of Search .......... 55/67, 197, 161, 162, 55/208, 28, 32

[56] References Cited

U.S. PATENT DOCUMENTS

| | | | |
|---|---|---|---|
| 2,753,950 | 7/1956 | Baker et al. | 55/162 |
| 3,002,583 | 10/1961 | Findlay | 55/67 |
| 3,156,548 | 11/1964 | Perry | 55/197 |
| 3,192,687 | 7/1965 | Silva et al. | 55/162 X |
| 3,267,646 | 8/1966 | Kauss et al. | 55/197 |
| 3,374,607 | 3/1968 | Fisher et al. | 55/67 |
| 3,550,429 | 12/1970 | MacMurtrie et al. | 55/197 X |
| 3,751,966 | 8/1973 | Ryan et al. | 73/23.1 |
| 3,841,059 | 10/1974 | McCabe | 55/197 |
| 3,926,589 | 12/1975 | Klementi et al. | 55/197 X |

OTHER PUBLICATIONS

Analytical Chemistry, vol. 45, No. 7, 6/1973, pp. 1236-1240, Schomburg et al. Article.

*Primary Examiner*—John Adee

[57] ABSTRACT

An apparatus and method for separating and collecting chromatographic samples in which three separate chromatographic columns are cycled through an elution mode, an elevated temperature back-flush mode, and a cooling back-flush mode in continuous repetition so that at any one time one of the columns is in an elution mode, another of the columns is in elevated temperature back-flush mode, and the remaining column is in cooling back-flush mode.

8 Claims, 1 Drawing Figure

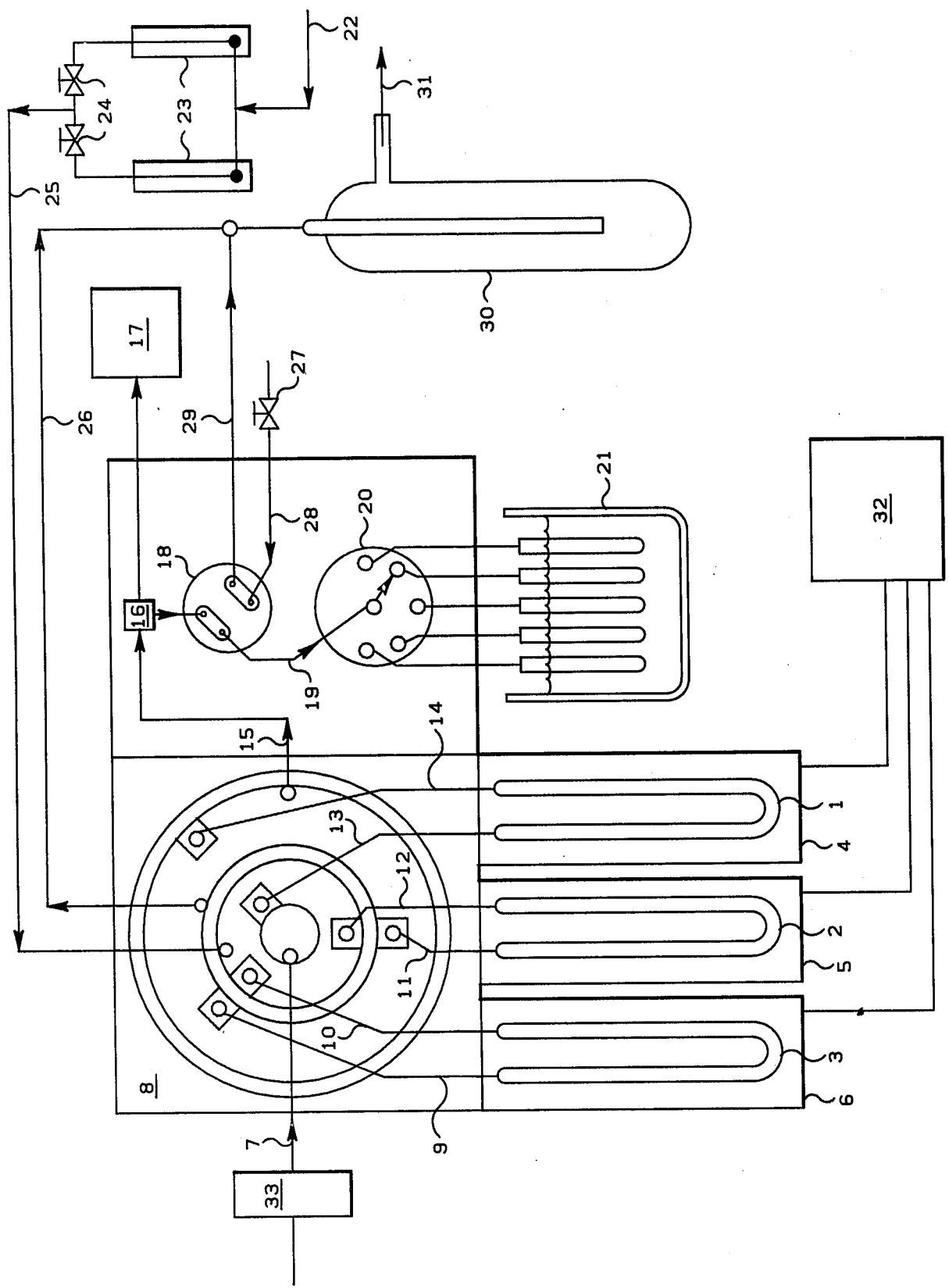

AUTOMATED TEMPERATURE PROGRAMMED PREPARATIVE CHROMATOGRAPHY

BACKGROUND OF THE INVENTION

This invention relates to chromatographic analysis. In one of its aspects this invention relates to an apparatus for separating and collecting chromatographic samples. In another of its aspects this invention relates to a method for separating and collecting chromatographic samples. In a specific aspect this invention relates to the collection and separation of gasoline fractions for analysis.

Many different techniques, procedures, and apparatuses are well-known in the art of gas-liquid chromatography. Automatic sample injectors, automatic fraction collectors, automatic temperature programmers, backflushing of columns, automated preparative gas chromatographs, and the like, are well-known in the art of gas-liquid chromatography. This invention, however, provides a unique arrangement for the simultaneous use of several well-known techniques, including backflushing of columns, to facilitate the repetitive running of samples and collection of fractions.

It is therefore an object of this invention to provide an apparatus for separating and collecting chromatographic samples which can be continuously operated with a sample being eluted from a chromatographic column while another chromatographic column is being back-flushed after an elution process and a third column is being back-flushed and cooled after the heated purge in a continuous cycle so that sample elution can be conducted with minimal interruption. It is also an object of this invention to provide a method for continuously eluting chromatographic sample using a combination of three chromatographic columns alternating through elution, heated back-flush, and cooling back-flush modes. It is another object of this invention to provide a method and apparatus for automatically separating and collecting chromatographic samples.

Other aspects, objects, and the various advantages of this invention will become apparent upon reading the specification, appended claims, and upon studying the drawing.

STATEMENT OF THE INVENTION

According to this invention an apparatus is provided for separating and collecting chromatographic samples. In the apparatus three separate chromatographic columns are each provided with means for temperature control. The columns are connected with the necessary lines and valving for supplying and removing sample or flushing gas for each of the columns. Means are supplied for automatically coordinating temperature and flow through the three columns so that one column is maintained at a programmed elution temperature and has sample gas passing therethrough while another column is maintained at a temperature elevated above the elution temperature and has flushing gas passing therethrough in the reverse direction from elution flow while the remaining column is cooled at least to elution temperature while flushing gas passes therethrough in the reverse direction from elution flow with a means for automatically sequencing the temperature and flow so that each column is cycled through elution flow, heated flush, and elution temperature flush seriatim. The reverse direction flow is generally known as backflushing. All flushing operations described in this specification are backflushing operations, although the invention broadly covers operation in which flushing of columns after elution entails flush flow in the same direction as elution flow.

A method is also supplied for separating and collecting chromatographic samples in which sample gas is passed through a first column maintained at elution temperature while flush gas is simultaneously passed through a second column maintained at a temperature elevated above elution temperature and flush gas is simultaneously passed through a third column maintained at a temperature that decreases at least to elution temperature with a sequencing of the change of flow through the first, second, and third columns so that each column is passed through a sequence of flow pattern in the order of sample elution followed by elevated temperature flush followed by elution temperature flush in continuous repetition.

This invention is a gas-liquid chromatographic apparatus for use in rapidly separating desired samples into fractions, and this method is a more efficient separation technique than conventional distillation for obtaining hydrocarbon fractions. This invention provides a means of simultaneously: (1) subjecting a sample to separation conditions in a packed column, (2) backflushing at elevated temperatures a packed column which has previously been used to separate a sample into fractions, said backflushing being employed for removal from the column of residues of the original sample which were not eluted from the column previously and, (3) backflushing a packed column in a cool-down cycle which had been previously employed in a separation step and had also been previously subjected to backflushing at elevated temperature. In a preferred embodiment, this invention provides a chromatographic apparatus containing three columns each in a separate oven such that simultaneously one column is employed in a separation mode, one column is operated in a backflushing mode at elevated temperature, and the third column is operated in a backflushing mode during a cool-down cycle. The apparatus of this invention can be operated manually, that is, with manual switching from mode to mode, with manual sample injection, and with manual selection of the fractions after elution from a column. However, it is preferred that the operation of this apparatus be handled automatically by use of a programmer or sequencer which will automatically inject sample at the appropriate time, switch a column from mode to mode at the appropriate time, and operate a sample collection device to collect the eluted fractions as separate products.

Referring now to the drawing, packed columns 1, 2, and 3 are the separation means of the inventive chromatographic separator. Columns 1, 2, and 3 can be fabricated from tubing or pipe of any desired length and diameter in any desired material. The columns are packed with any of the well-known packing materials used in the gas chromatographic art, such as a liquid coated onto a solid support such as a diatomaceous earth. Columns 1, 2, and 3 are arranged with temperature control means such as ovens 4, 5, and 6 which can be independently heated to a high temperature and subsequently cooled to the desired elution temperature. Ovens 4, 5, and 6 are connected to temperature programmer 32 which allows the columns to be individually maintained at any desired constant temperature or heated or cooled at any desired rate.

The sample to be analyzed and appropriate carrier gas, such as nitrogen or helium, are introduced into the chromatographic separator via sample injector 33 and thence through conduit 7 to sample/back-flush valve 8. In the drawing, column 1 is arranged in the sample separation mode, whereas columns 2 and 3 are arranged in the back-flush mode. Hence, the sample to be analyzed and the carrier gas flow into valve 8 and through conduit 13 into column 1. After flowing through packed column 1 and thus, being subjected to separation conditions, the separated sample and carrier gas flow from column 1 via conduit 14 back into valve 8 and therefrom via conduit 15 to detector 16. Detector 16 can be any of those well-known detectors in the chromatographic art, such as a thermal conductivity detector. The signal from detector 16 is recorded on recorder 17 which can be such as a strip chart recorder. After passing through detector 16, the sample and carrier gas proceed into by-pass valve 18 where, as desired, the stream passes via conduit 29 to trap 30 or via conduit 19 to sample selector valve 20 from which the sample fractions are colllected in appropriate vessels in sample collector 21.

While column 1 is operating in the sample separation mode, columns 2 and 3 are operating in the back-flush mode, wherein the desired backflushing gas, such as nitrogen or helium, is passed from line 22 through meters 23 and valves 24 and then through conduit 25 into sample/back-flush valve 8 and into columns 2 and 3 via conduits 12 and 10, respectively. After passing through columns 2 and 3 in a reverse direction compared to sample separation mode, the back-flush gas carries the heavy residue of the sample and is passed via conduits 9 and 11 back through valve 8 and then through conduit 26 to trap 30 where the back-flush gas and volatile components of the residue are vented at exit port 31.

The operation of sample/back-flush valve 8, by-pass valve 18, sample selector valve 20, temperature programmer 32, and sample injector 33 can be coordinated by a sequencer which initiates sample injection at the proper time into the one of the three columns 1, 2, or 3 which is in the sample separation mode, provides the appropriate temperature conditions in the column and diverts the appropriate sample fractions through by-pass valve 18 and through sample selector valve 20 into the appropriate collection vessels. Of the two columns which are in the back-flush mode, one is in a heating cycle while the other is in a cooling cycle. The effluent from the columns in the back-flush mode is collected in trap 30.

The chromatographic apparatus of this invention may be employed in the separation of any desired sample, collection of appropriate fractions thereof, and backflushing of the packed columns to remove the heavy and/or undesirable residue of the original sample from the columns. The apparatus of this invention may be employed for the separation of identical samples successively in order to build the volume of the appropriate fraction or of different samples successively in order to obtain the desired fractions of each. This apparatus can be employed for the collection of pure samples or for the collection of fractions which may consist of simple mixtures or of complex mixtures of components. It is especially preferred that this apparatus be employed in the separation of a gasoline fraction from the total effluent from a catalytic refining unit. For example, the effluent from a typical cracking unit will contain a complex mixture of hydrocarbons containing from 1 to approximately 40 carbon atoms per molecule. Using an elution temperature in the range of about 100° C. to 200° C., an elevated flushing temperature of about 200° C. to 300° C., and a cycle sequence in the range of about 5 to about 15 minutes, the apparatus of this invention is capable of separating cleanly from this effluent a representative fraction containing the compounds of from 3 to about 12 carbon atoms per molecule, or narrow fractions such as a $C_5$–$C_8$ light gasoline or a $C_7$–$C_9$ naphtha which can be directly employed as a gasoline, as a fuel-blending stock, or for further analysis using well-known analytical techniques, such as mass spectral/gas chromatographic analysis or gas chromatographic analysis.

We claim:
1. An apparatus for separating and collecting chromatographic samples said apparatus comprising:
    (a) three separate chromatographic columns each provided with means for temperature control;
    (b) containing lines and valving for supplying and removing samples and flushing gas to each of the columns;
    (c) means for automatically coordinating temperature and flow through the three columns so that, simultaneously, one column is maintained at a programmed elution temperature while sample gas is passed therethrough, another column is maintained at a temperature elevated above the elution temperature while a stream of flushing gas is passed therethrough, and the remaining column is maintained at a temperature decreasing to elution temperature while another stream of flushing gas is passed therethrough; and
    (d) means for automatically sequencing temperature control and flow so the each column is cycled through elution flow, heated flush, and decreasing to elution temperature flow seriatim.
2. An apparatus of claim 1 wherein each chromatographic column is in a separate chamber provided with means for temperature control.
3. An apparatus of claim 1 wherein the means for passing flushing gas directs flow of flushing gas in a direction countercurrent to that in which sample gas is passed.
4. A method for separating and collecting chromatographic samples said method comprising:
    (a) passing sample through a first column maintained at elution temperature;
    (b) simultaneously passing a stream of flush gas thorugh a second column maintained at a temperature elevated above elution temperature;
    (c) simultaneously passing another stream of flush gas through a third column maintained at a temperature decreasing to elution temperature; and
    (d) sequencing change of flow through said first, second, and third columns so that each column is passed thorugh a sequence of flow patterns in the order of sample elution followed by elevated temperature flush followed by elution temperature flush in continuous repetition.
5. A method of claim 4 wherein flushing gas is passed through the columns in a direction countercurrent to the flow of sample gas.
6. A method of claim 4 wherein there is automatic control and sequencing of temperatures and flush.
7. A method of claim 4 wherein the sample is a gasoline fraction, said elution temperature is in the range of about 100° C. to about 200° C. and said elevated temperature is in the range of about 200° C. to about 300° C.
8. A method of claim 6 wherein change of flow is sequenced to change about every 5 to 15 minutes.

* * * * *